United States Patent [19]

Sklar

[11] Patent Number: 5,861,432
[45] Date of Patent: Jan. 19, 1999

[54] GLYCOLIC ACID AND TRETINOIN FORMULATION FOR THE TREATMENT OF ACNE

[76] Inventor: Jerald L. Sklar, 9016 Green Oaks Cir., Dallas, Tex. 75243

[21] Appl. No.: 753,961

[22] Filed: Jan. 16, 1997

Related U.S. Application Data

[60] Provisional application No. 60/011,271 Feb. 7, 1996.
[51] Int. Cl.$^6$ ..................................................... A61K 31/19
[52] U.S. Cl. ..................... 514/557; 514/570; 514/775; 514/784; 514/857; 514/873
[58] Field of Search ..................................... 514/847, 873, 514/859, 725, 784, 557, 520

[56] References Cited

U.S. PATENT DOCUMENTS

| | | | |
|---|---|---|---|
| 5,153,230 | 10/1992 | Jaffery | 514/847 |
| 5,389,677 | 2/1995 | Yu et al. | |
| 5,549,888 | 8/1996 | Venkateswaran | 514/859 |

OTHER PUBLICATIONS

Chemical Abstracts AN 97:96580, Franchon et al, US Patent 5,679,374, Oct. 21, 1997.

Rosan, Alan, "The Chemistry of Alpha–Hydroxy Acids," A Supplement to Cosmetic Dermatology, Oct. 1994, pp. 4–20.

Jackson, Edward, "Do AHA Products Really Work," A Supplement to Cosmetic Dermatology, Oct. 1994, pp. 21–22.

Klein, Marvin, "Clinical Observation Remains Essential in Evaluating the Cosmetic Effectiveness of Glycolie Formulations;" A Supplement to Cosmetic Dermatology, Oct. 1994, pp. 35–36.

*Primary Examiner*—Keith D. MacMillan
*Attorney, Agent, or Firm*—David H. Judson

[57] ABSTRACT

A preparation for treating acne containing as active ingredients glycolic acid and tretinoin in an emollient base.

3 Claims, No Drawings

GLYCOLIC ACID AND TRETINOIN FORMULATION FOR THE TREATMENT OF ACNE

TECHNICAL FIELD

The present invention relates generally to a topical medication for treating acne and more particularly to a lotion adapted for treating acne vulgaris. This invention is based on Provisional Application No. 60/011,271, entitled "Glycolic Acid and Tretinoin Formulation For the Treatment of Acne" which was filed on Feb. 7, 1996.

BACKGROUND OF THE INVENTION

All-trans-retinoic-acid, known as tretinoin or Retin-A, is an extremely photosensitizing agent used for the treatment of normalizing skin since the 1970's. It works intracellularly, and it organizes the skin, exfoliates it and substantially changes the physiology.

Glycolic acid, an alpha-hydroxy acid, is used in many cosmetic products for improved skin appearance. There are two main theories on how glycolic acid works. The first theory proposes that the glycolic acid produces a mild subclinical irritation which stimulates the epidermis to produce fresh skin, while the second theory proposes that glycolic acid weakens the intercellular bonding of the corneocytes in a manner similar to both water and retinoids. Unfortunately, little objective data regarding the effectiveness of alpha-hydroxy acid has been published thereby leaving the industry to rely on anecdotal information which is difficult to quantify. It is quite clear that many of the topical cosmetics incorporating glycolic acid or other alpha-hydroxy acids have insufficient concentrations to accomplish their objectives.

As stated earlier, some alpha-hydroxy acids have been used in skin treatment. U.S. Pat. No. 4,107,330 discloses a preparation for the treatment of acne containing 0.1 to 10% by weight of thioglycolic acid and the salts, esters, and acid amides thereof, in the treatment of acne. The referenced acne treatment is premised on a sulfur based alpha-hydroxy acid and is not combined with tretinoin.

Since the exact workings of glycolic acid in affecting the skin is unclear, doctors have been reluctant to apply glycolic acid and tretinoin at similar times on patients. Albert Kligman's article "Compatibility of A Glycolic Acid Cream with Topical Tretinoin for the Treatment of the Photo Damaged Face of Older Women" made a tentative conclusion that a topical 8% glycolic acid cream could be used in conjunction with tretinoin to treat photoaged facial skin. Kligman's uncontrolled study required that the subjects apply glycolic acid in the morning and, after washing with Dove® soap, apply tretinoin at night. Kligman's experiment required separate applications of the two compounds during the day and the two compounds did not simultaneously overlap any skin sites.

Jonathan Weiss and Joel Shavin conducted a similar experiment that is outlined in their article "An Evaluation of the Compatibility of Tretinoin Cream 0.05% and a Glycolic Acid 8% Solution For Acne Prone Skin." They conducted a comparative experiment between tretinoin applied alone, glycolic acid applied alone, and a combination of tretinoin and glycolic acid, each applied separately at different times during the day. The experiment indicated that the effectiveness of tretinoin was not enhanced with the concomitant use of the glycolic acid solution although the tretinoin alone or in combination was superior to the glycolic acid alone.

Accordingly, both glycolic acid and tretinoin, while, in one instance, having been found to have utility in treating photoaged skin through separate treatments during the day, have not been used as a treatment for acne through a cream combining both compounds.

It is thus an object of the present invention to produce a treatment for and inhibition of acne which needs only to be applied once a day combining glycolic acid and tretinoin.

SUMMARY OF THE PRESENT INVENTION

It is a feature of the present invention to provide a lotion for use on the skin which prevents and treats acne and, more specifically, acne vulgaris. In one embodiment of the invention for the treatment of acne, the invention entails applying to a situs of the acne a composition comprising about 10% by weight of glycolic acid and 0.025% of tretinoin acid dispersed in an emollient base and allowing the composition to remain essentially intact until the next application period.

The theory behind the combination of these two compounds is that both work in a similar manner as far as exfoliation and re-regulation of follicular keratinazation. Based on clinical observations, the combination of both compounds has produced a synergistic effect in treating acne, including acne vulgaris. Other embodiments of the invention could extend the treatment to various other skin conditions, such as lentigos, melasma and actinic keratoses.

DETAILED DESCRIPTION

The present acne treatment utilizes a composition comprising a glycolic acid and tretinoin acid dispersed in a semi-solid emollient base. Glycolic acid is an alpha-hydroxy acid which are organic carboxylic acids having one hydroxyl group attached to the alpha position of the carboxylic carbon atom.

The human skin is comprised of two principal components, the avascular epidermis and the underlying vascular dermis. The epidermis consists of four layers: the stratum corneum, stratum granulosum, stratum spinosum and stratum basale. The dermis mainly consists of collagen, elastin fibers and ground substances including glycosaminoglycan. There are two forms of skin aging: intrinsic aging, also known as chronological aging and extrinsic aging, also known as photoaging. The aging process normally involves the dermis.

Intrinsic aging is a degenerative process attributed to declining physiologic functions and capacities. Extrinsic aging is caused by external factors such as sunlight, radiation, air pollution, etc. AHAs have been used topically in the prior art on keratinization (epidermal layer) where the effects are clinically detectable by the formation of a new stratum corneum. AHAs also have dermal effects. Topical application of AHAs have caused increased amounts of mucopolysacchardies and collagen and increased skin thickness without detectable inflammation. The benefits of the AHA have caused them to be incorporated into cosmetic products for purposes such as cleansing, conditioning, dry skin etc.

AHAs are categorized as nontoxic and have been used as skin desquamative agents, especially in routine use for acne, wrinkles, photoaged skin and pigmented disorders. The acidity of the AHAs is not a proven indicator of their potency.

AHAs work as a topical application that works as a local irritant. Tretinoin, on the other hand, functions intracellularly and can serve to normalize cells with dysfunction. Tretinoin changes the cellular configuration of the skin and, in the process, makes the skin more organized, exfoliates and substantially changes the physiology. Tretinoin applications also causes increased sensitivity forcing the use among patients of powerful sun blocks.

As stated earlier, there have been experiments conducted using 8% glycolic acid cream in a treatment regime with topical tretinoin. The protocol was to wash one's face in the morning with Dove® apply the glycolic acid to the face in the morning, wash the face with Dove® soap at night, pat the face dry and then apply tretinoin.

Based on the prior art, there is some belief that the acidity of the AHAs would reduce the efficacy of a simultaneous tretinoin application or even of a non-simultaneous tretinoin application. Therefore, this invention runs counter to the prior art by focusing on deriving synergistic effects from an application containing both glycolic acid and tretinoin. By simultaneously treating the skin at two levels, it is theorized that enhanced skin promotion will occur. There is some indication that the negative side effects individually attached to these compounds are diminished by this combination.

The inventor has obtained clinical observation on over forty patients which were administered various formulations of tretinoin combined with glycolic acid. The patients were afflicted with a variety of conditions, including acne vulgaris, lentigos, melasma, wrinkles, actinic damage and actinic keratosis. The tretinoin concentration ranged from 0.025% to 0.1% by weight while the glycolic acid concentration ranged from 5–15% by weight. The formulations were kept in the pH ranges of 1.0–2.0. In terms of efficacy, the optimal rate seemed to be a tretinoin concentration of 0.025% and a glycolic acid concentration of 10%. Due to the low pH range, several patients have observed "stinging" and "burning" for 5–10 minutes after application of the product. A majority of these patients became acclimated to the sensation after one or two weeks.

The semi-solid emollient base in which the glycolic acid and tretinoin are dispersed may be any such material conventionally used as a vehicle for medicinal substances for topical application. The preferred method of producing the topical medication is to generate the base which includes BHT, which prevents deactivation of tretinoin, add tretinoin to the base, and then add the glycolic acid.

Additional ingredients which may be present in the composition include: Polyoxyl 40 stearate, which is a thickener that allows the drug to penetrate the skin; other thickeners such as stearic acid, cetyl alcohol, stearyl alcohol, and xanthene gum; sorbic acid, which acts as a preservative and pH enhancer; isopropyl myristate, which is a skin moisturizer that softens up the keratin layer; and purified water. The additional ingredients may be present in total amounts of up to about ninety (90) percent by weight. The preferred pH of the composition is 1.4 which increases the activity of the glycolic acid component.

The viscosity of the compositions used herein has not been found to be critical, and thus the specific viscosity of the composition will be selected merely as a matter of convenience.

Preliminary results indicate that the majority of patients report superior results over other prescription products, including tretinoin and glycolic acid alone. For treatment of acne, the combination has been effective in treating those with open and closed comedones. In addition, patients with actinic damage and wrinkles have reported favorably on the effectiveness of the combination.

It should be appreciated by those skilled in the art that the specific embodiments disclosed above may be readily utilized as a basis for modifying or designing other formulations for carrying out the same purposes of the present invention.

I claim:

1. A method for treating acne by applying to an affected skin a preparation containing, in weight percent, about 10% glycolic acid, about 0.025–1.0% tretinoin, and a pharmacologically acceptable carrier.

2. A composition suitable for use in treating acne, comprising:

about 10–15% glycolic acid;

about 0.025–1.0% tretinoin; and an emollient base.

3. A composition suitable for treating skin conditions derived from chronic sun exposure, comprising:

about 10–15% glycolic acid;

about 0.05% tretinoin; and an emollient base.

* * * * *